(12) United States Patent
Sher

(10) Patent No.: US 9,149,457 B2
(45) Date of Patent: Oct. 6, 2015

(54) NUTRACEUTICAL COMPOSITION FOR PDE4 INHIBITION, ENHANCED DOPAMINE METABOLISM AND LONG TERM POTENTIATION

(71) Applicant: Justin Sher, Woodside, CA (US)

(72) Inventor: Justin Sher, Woodside, CA (US)

(*) Notice: Subject to any disclaimer, the term of this patent is extended or adjusted under 35 U.S.C. 154(b) by 0 days.

(21) Appl. No.: 14/499,143

(22) Filed: Sep. 27, 2014

(65) Prior Publication Data

US 2015/0093458 A1    Apr. 2, 2015

Related U.S. Application Data

(60) Provisional application No. 61/883,433, filed on Sep. 27, 2013, provisional application No. 62/046,953, filed on Sep. 6, 2014, provisional application No. 62/047,055, filed on Sep. 7, 2014.

(51) Int. Cl.

| | | |
|---|---|---|
| A61K 31/352 | (2006.01) | |
| A61K 31/221 | (2006.01) | |
| A61K 31/353 | (2006.01) | |
| A61K 36/28 | (2006.01) | |
| A61K 31/198 | (2006.01) | |
| A61K 31/4415 | (2006.01) | |
| A61K 31/4525 | (2006.01) | |
| A23L 1/30 | (2006.01) | |
| A23L 1/305 | (2006.01) | |
| A23L 1/302 | (2006.01) | |
| A61K 9/48 | (2006.01) | |

(52) U.S. Cl.
CPC ............ *A61K 31/352* (2013.01); *A23L 1/30* (2013.01); *A23L 1/3002* (2013.01); *A23L 1/302* (2013.01); *A23L 1/3051* (2013.01); *A61K 9/48* (2013.01); *A61K 31/198* (2013.01); *A61K 31/221* (2013.01); *A61K 31/353* (2013.01); *A61K 31/4415* (2013.01); *A61K 31/4525* (2013.01); *A61K 36/28* (2013.01); *A23V 2002/00* (2013.01)

(58) Field of Classification Search
None
See application file for complete search history.

(56) References Cited

U.S. PATENT DOCUMENTS

| 6,436,946 B1 * | 8/2002 | Mann ................ 514/263.31 |
|---|---|---|
| 2008/0044390 A1 | 2/2008 | Jin |
| 2009/0048339 A1 | 2/2009 | Kanwar |
| 2011/0020443 A1 | 1/2011 | Liu |
| 2011/0064712 A1 * | 3/2011 | Amato ................ 424/94.2 |
| 2011/0159048 A1 | 6/2011 | Crain |
| 2011/0177097 A1 | 7/2011 | Shulman |
| 2012/0041045 A1 | 2/2012 | Harvey |
| 2012/0121743 A1 | 5/2012 | Garnier |

FOREIGN PATENT DOCUMENTS

| WO | 2007123699 A1 | 11/2007 |
|---|---|---|
| WO | 2008153426 A1 | 12/2008 |

OTHER PUBLICATIONS

"Chemically induced LTP?" on Longecity.org (http://www.longecity.org/forum/topic/51732-chemically-induced-ltp/—post by abelard lindsay on Mar. 14, 2013).*
"NOW Foods" website (https://web.archive.org/web/20120318064725/http://www.nowfoods.com/Supplements/Products-by-Category/Herbs-Mushrooms/Extracts/M092515.htm)—web archived version from Mar. 18, 2012.*
K Shimoi et al: Intestinal absorption of luteolin and luteolin 7-O-beta-glucoside in rats and humans. FEBS Lett. 1998; 438(3):220-4.
SM Wittemer et al: Bioavailability and pharmacokinetics of caffeoylquinic acids and flavonoids after oral administration of Artichoke leaf extracts in humans. Phytomedicine. 2005; 12(1-2):28-38. abstract only.
A Perez et al: The flavonoid quercetin induces acute vasodilator effects in healthy volunteers: Correlation with beta-glucuronidase activity. Pharmacol Res. 2014; 89C:11-18. abstract only.
K Shimoi et al: Deglucuronidation of a flavonoid, luteolin monoglucuronide, during inflammation. Drug Metab Dispos. 2001; (12):1521-4.
SP Lin et al: Pharmacokinetics and tissue distribution of resveratrol, emodin and their metabolites after intake of Polygonum cuspidatum in rats. J Ethnopharmacol. 2012;;144(3):671-6. abstract only.
Y Kawai: β-Glucuronidase activity and mitochondrial dysfunction: the sites where flavonoid glucuronides act as anti-inflammatory agents. J Clin Biochem Nutr. 2014; 54(3):145-50.
O Tohyama et al: Klotho is a novel beta-glucuronidase capable of hydrolyzing steroid beta-glucuronides. J Biol Chem. 2004; 279(11):9777-84.
G Shoba et al: Influence of piperine on the pharmacokinetics of curcumin in animals and human volunteers. Planta Med. 1998; 64(4):353-6. abstract only.
JJ Johnson et al. Enhancing the bioavailability of resveratrol by combining it with piperine. Mol Nutr Food Res. 2011; 55(8):1169-76.
Post #1142 on Longecity: Bioscience, Health & Nutrition: Brain Health by "jadamgo" Feb. 7, 2013—06:40 AM retrieved from http://www.longecity.org/forum/topic/51732-chemically-induced-ltp/page-39#entry564700Post #1173 on Longecity: Bioscience, Health & Nutrition: Brain Health by "jadamgo" Feb. 12, 2013—07:38 PM downloaded from http://www.longecity.org/forum/topic/51732-chemically-induced-ltp/page-40#entry566063.

(Continued)

*Primary Examiner* — Susan Hoffman
(74) *Attorney, Agent, or Firm* — Berliner & Associates

(57) ABSTRACT

A nutritional supplement for increasing cognitive functioning. The supplement includes a flavonoid such as luteolin and a labdane diterpene such as forskolin. The supplement can also include one or any combination of L-phenylalanine, L-carnitine, acetyl-L-carnitine, and vitamin B6. Artichoke extract can be used as a source of luteolin. Methods of using the nutritional supplements to increase cognitive functioning are also included.

13 Claims, 2 Drawing Sheets

(56) References Cited

OTHER PUBLICATIONS

Post #1173 on Longecity: Bioscience, Health & Nutrition: Brain Health by "jadamgo" Feb. 12, 2013—07:38 PM downloaded from http://www.longecity.org/forum/topic/51732-chemically-induced-ltp/page-40#entry566063.
Post #59 on Longecity: Bioscience, Health & Nutrition: Brain Health by "abelard lindsay" May 5, 2012—01:37 PM retrieved from http://www.longecity.org/forum/topic/51732-chemically-induced-ltp/page-2#entry513884.
Post #862 on Longecity: Bioscience, Health & Nutrition: Brain Health by "zrbarnes" Oct. 12, 2012—03:47 PM retrieved from http://www.longecity.org/forum/topic/51732-chemically-induced-ltp/page-29#entry539892.
Post #2165 on Longecity: Bioscience, Health & Nutrition: Brain Health by "magta39" Nov. 26, 2013—08:25 PM retrieved from http://www.longecity.org/forum/topic/51732-chemically-induced-ltp/page-73#entry626025.
Post #1464 on Longecity: Bioscience, Health & Nutrition: Brain Health by "chung_pao" Apr. 23, 2013—06:52 PM retrieved from http://www.longecity.org/forum/topic/51732-chemically-induced-ltp/page-49#entry581824.
Post on Slate Star Codex by "Scott Alexander" entitled "Nootropics Survey Results and Analysis" Feb. 16, 2014 on Slate Star Codex retrieved from http://slatestarcodex.com/2014/02/16/nootropics-survey-results-and-analysis.
International Search Report re PCT/US2014/057923 dated Sep. 2, 2015.
K Rutten et al: Phosphodiesterase Inhibitors Enhance Object Memory Independent of Cerebral Blood Flow and Glucose Utilization in Rats; Neuropsychopharmacology (2009) 34, pp. 1914-1925.
T Egawa et al: Rolipram and Its Optical Isomers, Phosphodiesterase 4 Inhibitors, Attenuated the Scopolamine- Induced Impairments of Learning and Memory in Rats; Jpn. J. Pharmacol. 75, pp. 275-281 (1997).
HT Zhang et al: Effects of rolipram on scopolamine-induced impairment of working and reference memory in the radial-arm maze tests in rats; Psychopharmacology (Berl). Jun. 2000; 150(3): pp. 311-316. Abstract Only.
HT Zhang et al: Inhibition of Cyclic AMP Phosphodiesterase (PDE4) Reverses Memory Deficits Associated with NMDA Receptor Antagonism; Neuropsychopharmacology 2000 vol. 23 No. 2, pp. 198-204.
HT Zhang et al: Effects of the novel PDE4 inhibitors MEM1018 and MEM1091 on memory in the radial-arm maze and inhibitory avoidance tests in rats; Psychopharmacology (Berl). May 2005;179(3):613-9. Epub Jan. 26, 2005. Abstract Only.
C Wang et al: The phosphodiesterase-4 inhibitor rolipram reverses Aβ-induced cognitive impairment and neuroinflammatory and apoptotic responses in rats; Int J Neuropsychopharmacol. Jul. 2012;15(6):pp. 749-766. doi: 10.1017/S1461145711000836. Epub Jun. 9, 2011.Abstract Only.
GM Rose et al: Phosphodiesterase inhibitors for cognitive enhancement; Curr Pharm Des. 2005;11(26): PP3329-34. Abstract Only.
J Drott et al: Etazolate improves performance in a foraging and homing task in aged rats; Eur J Pharmacol. May 25, 2010;634(1-3):pp. 95-100. doi: 10.1016/j.ejphar.2010.02.036. Epub Mar. 17, 2010.Abstact Only.
Lx Li et al: Prevention of cerebral ischemia-induced memory deficits by inhibition of phosphodiesterase-4 in rats; Metab Brain Dis. Mar. 2011;26(1):pp. 37-47. doi: 10.1007/s11011-011-9235-0. Epub Feb. 17, 2011 Abstract Only.
M Gallant et al: Discovery of MK-0952, a selective PDE4 inhibitor for the treatment of long-term memory loss and mild cognitive impairment; Bioorg Med Chem Lett. Nov. 15, 2010;20(22):pp. 6387-6393. doi: 10.1016/j.bmcl.2010.09.087. Epub Sep. 21, 2010. Abstract Only.
RJ Heaslip et al: Emetic, central nervous system, and pulmonary activities of rolipram in the dog. Eur J Pharmacol. Nov. 24, 1995;286(3):pp. 281-290. Abstract Only.

O Bruno et al: GEBR-7b, a novel PDE4D selective inhibitor that improves memory in rodents at non-emetic doses; British Journal of Pharmacology (2011) 164 pp. 2054-2063.
S Mackenzie et al: Action of rolipram on specific PDE4 cAMP phosphodiesterase isoforms and on the phosphorylation of cAMP-response-element-binding protein (CREB) and p38 mitogen-activated protein (MAP) kinase in U937 monocytic cells; Biochem. J. (2000) 347, pp. 571-578 (Printed in Great Britain).
W Xu et al: Individual CREB-target genes dictate usage of distinct cAMP-responsive coactivation mechanisms; EMBO J. Jun. 20, 2007; 26(12): pp. 2890-2903. Published online May 24,2007. doi: 10.1038/sj.emboj.7601734.
E Benito et al: cAMP Response Element-Binding Protein Is a Primary Hub of Activity-Driven Neuronal Gene Expression; The Journal of Neuroscience, Dec. 14, 2011 • 31(50): pp. 18237-18250.
J Lee et al: Mitochondrial Cyclic AMP Response Element-binding Protein (CREB) Mediates Mitochondrial Gene Expression and Neuronal Survival; J Biol Chem. Dec. 9, 2005; 280(49): pp. 40398-40401. doi:10.1074/jbc.C500140200.
K Deisseroth et al: Signaling from Synapse to Nucleus: Postsynaptic CREB Phosphorylation during Multiple Forms of Hippocampal Synaptic Plasticity; Neuron, vol. 16, pp. 89-101, Jan. 1996.
S Kida: A Functional Role for CREB as a Positive Regulator of Memory Formation and LTP; Exp Neurobiol. Dec. 2012; 21(4): pp. 136-140.
A Suzuki et al: Behavioral/Systems/Cognitive Upregulation of CREB-Mediated Transcription Enhances Both Short-and Long-Term Memory; J. Neurosci., Jun. 15, 2011, 31(24): pp. 8786-8802.
HPT Ammon et al: Forskolin : From an Ayurvedic Remedy to a Modern Agent; Planta Medica 1985 pp. 473-477.
KB Seamon et al: Forskolin: a unique diterpene activator of cyclic AMP-generating systems; J Cyclic Nucleotide Res. 1981;7(4): pp. 201-224 Abstract Only.
M Barad et al: Rolipram, a type IV-specific phosphodiesterase inhibitor, facilitates the establishment of long-lasting long-term potentiation and improves memory; Proc. Natl. Acad. Sci. USA, vol. 95, pp. 15020-15025, Dec. 1998.
MC Yu et al: Luteolin, a non-selective competitive inhibitor of phosphodiesterases 1-5, displaced [3H]-rolipram from high-affinity rolipram binding sites and reversed xylazine/ketamine-induced anesthesia; Eur J Pharmacol. Feb. 10, 2010;627(1-3): pp. 269-275 Abstract Only.
AL Chan et al: Inhibitory effects of quercetin derivatives on phosphodiesterase isozymes and high-affinity [(3) H]—rolipram binding in guinea pig tissues; Invest New Drugs. Oct. 2008;26(5): pp. 417-424 Abstract Only.
L Yang et al: Hesperidin-3-O-Methylether Is More Potent than Hesperidin in Phosphodiesterase Inhibition and Suppression of Ovalbumin-Induced Airway Hyperresponsiveness; Evidence-Based Complementary and Alternative Medicine, vol. 2012, Article ID 908562, 12 pages.
S-J Park et al: Resveratrol Ameliorates Aging-Related Metabolic Phenotypes by Inhibiting cAMP Phosphodiesterases; Cell. Feb. 3, 2012; 148(3): pp. 421-433.
W-C Ko et al: Biochanin A, a Phytoestrogenic Isoflavone with Selective Inhibition of Phosphodiesterase 4, Suppresses Ovalbumin-Induced Airway Hyperresponsiveness; Evidence-Based Complementary and Alternative Medicine, vol. 2011, Article ID 635058, 13 pages.
MR Nichols et al: Tyrosine kinase-independent inhibition of cyclic-AMP phosphodiesterase by genistein and tyrphostin 51; Arch Biochem Biophys. Jun. 15, 1999;366(2): pp. 224-230 Abstract Only.
Al Harvey et al: Pharmacological actions of the South African medicinal and functional food plant Sceletium tortuosum and its principal alkaloids; J Ethnopharmacol. Oct. 11, 2011;137(3): pp. 1124-1129 Abstract Only.
JE Brown et al: Luteolin-rich artichoke extract protects low density lipoprotein from oxidation in vitro; Free Radic Res. Sep. 1998;29(3):pp. 247-255 Abstract Only.
MC Yu et al: Luteolin, a non-selective competitive inhibitor of phosphodiesterases 1-5, displaced [3H]-rolipram from high-affinity

(56) References Cited

OTHER PUBLICATIONS rolipram binding sites and reversed xylazine/ketamine-induced anesthesia; Eur J Pharmacol. Feb. 10, 2010;627(1-3):pp. 269-275 (Epub Oct. 22, 2009) Abstract Only.
Y Kitagawa et al: Prediction and validation of a mechanism to control the threshold for inhibitory synaptic plasticity; Molecular Systems Biology 5:280 (2009); pp. 1-16.
D Puzzo et al: Role of phosphodiesterase 5 in synaptic plasticity and memory; Neuropsychiatric Disease and Treatment 2008:4(2) pp. 371-387.
N Otmakhov et al: Forskolin-Induced LTP in the CA1 Hippocampal Region Is NMDA Receptor Dependent; J Neurophysiol 91:1955-1962, 2004 (First published Dec. 31, 2003).
KM Piech-Dumas: CREB mediates the cAMP-responsiveness of the tyrosine hydroxylase gene: use of an antisense RNA strategy to produce CREB-deficient PC12 cell lines; Brain Res Mol Brain Res. Jul. 5, 1999;70(2): pp. 219-230 Abstract Only.
SC Kumer et al: Intricate regulation of tyrosine hydroxylase activity and gene expression; J Neurochem. Aug. 1996;67 (2):pp. 443-462 Abstract Only.
A Slominski et al: L-tyrosine and L-DOPA as hormone-like regulators of melanocytes functions; Pigment Cell Melanoma Res. Jan. 2012 ; 25(1): pp. 14-27.
A Amadasi et al: Pyridoxal 5'-phosphate enzymes as targets for therapeutic agents; Curr Med Chem. 2007;14(12): pp. 1291-1324 Abstract Only.
BF Curtin et al: Forskolin, an inducer of cAMP, up-regulates acetylcholinesterase expression and protects against organophosphate exposure in neuro 2A cells; Mol Cell Biochem. Oct. 2006;290(1-2):pp. 23-32 (Epub Aug. 19, 2006) Abstract Only.
P Hartvig et al: Reversal of postoperative somnolence using a two-rate infusion of physostigmine; Acta Anaesthesiol Scand. Nov. 1989; 33(8): pp. 681-685.
HL White et al: Acetyl-L-carnitine as a precursor of acetylcholine Neurochem Res. Jun. 1990;15(6):pp. 597-601 Abstract Only.
JH Chung: Metabolic benefits of inhibiting cAMP-PDEs with resveratrol; Adipocyte 1:4, pp. 256-258; Oct./Nov./Dec. 2012.
RH, Alasbahi et al: Forskolin and derivatives as tools for studying the role of cAMP; Pharmazie. Jan. 2012;67(1): pp. 5-13 Abstract Only.
DE Matthews: An Overview of Phenylalanine and Tyrosine Kinetics in Humans; J Nutr. Jun. 2007; 137(6 Suppi 1): pp. 1549S-1575S.
HC Lichtstein et al: Function of the vitamin B6 group; pyridoxal phosphate (codecarboxylase) in transamination: J Bioi Chem. 161 (1): pp. 311-320, 1945.
PJ Rani et al: Protective efficacy of L-carnitine on acetylcholinesterase activity in aged rat brain; J Gerontal A Bioi Sci Med Sci. 2001 \Mar;56(3) pp:B 140-1 Abstract Only.
RF Villa et al: ATP-ases of synaptic plasma membranes in striatum:Enzymatic systems for synapses functionality by in vivo administration of 1-acetylcarnitine in relation to Parkinson's Disease; Neuroscience. Jun. 25, 2013;248C:pp. 414-426. [Epub ahead of print] Abstract Only.
B Gong et al: Persistent improvement in synaptic and cognitive functions in an Alzheimer mouse model after rolipram treatment; J Clin Invest. Dec. 2004;114(11):pp. 1624-1634.
P Voisin et al: Cyclic AMP-dependent regulation of tyrosine hydroxylase mRNA and immunofluorescence levels in rat retinal precursor cells; Cell Tissue Res. May 2013;352(2): pp. 207-216 (Epub Jan. 26, 2013) Abstract Only.
CILTEP White Paper by "Abelard Lindsay" copyright 2013 by Natureal Stacks LLC, retrieved from https://www.upgradedself.com/files/ciltep-white-paper.pdf.
JH McLean et al: A phosphodiesterase inhibitor, cilomilast, enhances cAMP activity to restore conditioned odor preference memory after serotonergic depletion in the neonate rat; Neurobiol Learn Mem. Jul. 2009;92(1):pp. 63-69. doi: 10.1016/j.nlm.2009.02.003. Epub Feb. 20, 2009. Abstract Only.
Printout from the raysahelian.com website, "Artichoke leaf extract supplement health benefit, side effects—Use for cholesterol, IBS, and other medical conditions," Jan. 12, 2015, Ray Sahelian, pp. 1-7.

Printout from examine.com website, "Artichoke Extract—Scientific Review on Usage, Dosage, Side Effects," pp. 1-16. accessed Jun. 18, 2015.
Printout from drugs.com website, "Forskolin Uses, Benefits & Side Effects," 2009 Wolters Kluwer Health, pp. 1-2. accessed Jun. 18, 2015.
Printout from examine.com website,"Coleus forskohlii—Scientific Review on Usage, Dosage, Side Effects," pp. 1-18. accessed Jun. 18, 2015.
Post #1510 by "chung_pao" dated May 7, 2013—08:16 PM in www.longecity.org/forum/topic/51732-chemically-induced-ltp Re: Chemically induced LTP?
Post #1526 by "chung_pao" dated May 11, 2013—02:55 PM in www.longecity.org/forum/topic/51732-chemically-induced-ltp Re: Chemically induced LTP?
Post #1616 by "chung_pao" dated Jun. 27, 2013—11:39 PM in www.longecity.org/forum/topic/51732-chemically-induced-ltp Re: Chemically induced LTP?
Post #1653 by "chung_pao" dated Jul. 6, 2013—03:22 PM in www.longecity.org/forum/topic/51732-chemically-induced-ltp Re: Chemically induced LTP?
Post #1665 by "chung_pao" dated Jul. 11, 2013—02:37 AM in www.longecity.org/forum/topic/51732-chemically-induced-ltp Re: Chemically induced LTP?
Post #1667 by "chung_pao" dated May 7, 2013—08:16 PM in www.longecity.org/forum/topic/51732-chemically-induced-ltp Re: Chemically induced LTP?
Post #1728 by "chung_pao" dated Jul. 30, 2013—07:47 PM in www.longecity.org/forum/topic/51732-chemically-induced-ltp induced-ltp Re: Chemically induced LTP?
Post #1897 by "chung_pao" dated Sep. 14, 2013—10:16 PM in www.longecity.org/forum/topic/51732-chemically-induced-ltp Re: Chemically induced LTP?
Post #2173 by "chung_pao" dated Nov. 28, 2013—02:56 PM in www.longecity.org/forum/topic/51732-chemically-induced-ltp Re: Chemically induced LTP?
Post #1 by abelard lindsay dated #1 as updated and edited on Mar. 14, 2013, Apr. 9, 2013, Jun. 13, 2013, Jun. 21, 2013, Jun. 27, 2013, Sep. 10, 2013, Oct. 2, 2013, Nov. 24, 2013, and Mar. 12, 2014, and edited by abelard lindsay on Mar. 14, 2014—03:22 PM in www.longecity.org/forum/topic/51732-chemically-induced-ltp Re: Chemically induced LTP?
Post #75 by health_nutty dated May 10, 2012—05:31 PM in www.longecity.org/forum/topic/51732-chemically-induced-ltp Re: Chemically induced LTP?
Post #121 "abelard lindsay" dated May 20, 2012—07:27 PM in www.longecity.org/forum/topic/51732-chemically-induced-ltp Re: Chemically induced LTP?
Post #173 by "vali" dated May 25, 2012—01:15 AM in www.longecity.org/forum/topic/51732-chemically-induced-ltp Re: Chemically induced LTP?
Post #176 by "abelard lindsay" dated May 25, 2012—09:12 AM in www.longecity.org/forum/topic/51732-chemically-induced-ltp Re: Chemically induced LTP?
Post #195 by "ansatz22" dated May 28, 2012—08:25 PM in www.longecity.org/forum/topic/51732-chemically-induced-ltp Re: Chemically induced LTP?
Post #196 by "abelard lindsay" dated May 28, 2012—09:27 PM in www.longecity.org/forum/topic/51732-chemically-induced-ltp Re: Chemically induced LTP?
Post #197 zrbarnes dated Posted May 28, 2012—09:35 PM in www.longecity.org/forum/topic/51732-chemically-induced-ltp Re: Chemically induced LTP?
Post #205 by "abelard lindsay" dated Nov. 28, 2013—02:56 PM in www.longecity.org/forum/topic/51732-chemically-induced-ltp Re: Chemically induced LTP?
CREB From Wikipedia, the free encyclopedia, retrieved Sep. 26, 2012 5:44 AM from http://en.wikipedia.org/wiki/CREB.
Forskolin-Induced LTP in the CA1 Hippocampal Region Is NMDA Receptor Dependent Nikolai Otmakhov , Lena Khibnik , Nonna Otmakhova , Stephen Carpenter , Shervin Riahi , Brent Asrican , John

(56) References Cited

OTHER PUBLICATIONS

Lisman: Journal of Neurophysiology Published May 1, 2004 vol. 91 No. 5, 1955-1962 DOI: 10.1152/jn.00941.2003.
Long-term potentiation (neuroscience) from Wikipedia, the free encyclopedia, retrieved Aug. 26, 2014, 8:25 AM from http://en.wikipedia.org/wiki/Long_term_potentiation.
Nutraceutical From Wikipedia, the free encyclopedia, retrieved Sep. 26, 2012 5:53 AM from http://en.wikipedia.org/wiki/Nutraceutical.
Post #212 by "X_Danny_X" dated May 31, 2012—08:23 PM in www.longecity.org/forum/topic/51732-chemically-induced-ltp Re: Chemically induced LTP?.
Post #253 by X_Danny_X dated Jun. 2, 2012—04:31 AM in www.longecity.org/forum/topic/51732-chemically-induced-ltp Re: Chemically induced LTP?.
Post #257 by medievil dated Jun. 2, 2012—06:15 AM in www.longecity.org/forum/topic/51732-chemically-induced-ltp Re: Chemically induced LTP?.
Post #297 by middpanther88 dated Jun. 8, 2012—02:07 AM in www.longecity.org/forum/topic151732-chemically-induced-ltp Re: Chemically induced LTP.
Post #300 by trip96 dated Jun. 8, 2012—02:59 AM in www.longecity.org/forum/topic/51732-chemically-induced-ltp Re: Chemically induced Ltp?.
Post #315 by nupi dated Jun. 10, 2012—06:16 PM in www.longecity.org/forum/topic/51732-chemically-induced-ltp Re: Chemically induced LTP?.
Post #377 X_by Danny_X dated Jun. 28, 2012—02:06 AM in www.longecity.org/forum/topic/51732-chemicallyinduced-ltp Re: Chemically induced Ltp?.
Post #458 by gbpackers dated Jul. 9, 2012—05:46 AM in www.longecity.org/forum/topic/51732-chemically-induced-ltp Re: Chemically induced LTP?.
Post #460 by zrbarnes dated Jul. 19, 2012—08:53 AM in www.longecity.org/forum/topic/51732-chemically-induced-ltp Re: Chemically induced LTP?.
Post #462 by gbpackers dated Jul. 19, 2012—03:56 PM in www.longecity.org/forum/topic/51732-chemically-inducedltp Re: Chemically induced LTP?.
Post #636 by IA87 dated Aug. 20, 2012—07:26 PM in www.longecity.org/forum/topic/51732-chemically-induced-ltp Re: Chemically induced LTP?.
Post #638 by unbeatableking dated Aug. 20, 2012—07:57 PM in www.longecity.org/forumltopic/51732-chemically-induced-ltp Re: Chemically induced LTP?.
Post #205 by "abelard lindsay" dated May 29, 2012—03:59 PM in www.longecity.org/forumltopic/51732-chemicallyinduced-ltp Re: Chemically induced LTP?.

* cited by examiner (A)

(B)

(C)

(D)

NUTRACEUTICAL COMPOSITION FOR PDE4 INHIBITION, ENHANCED DOPAMINE METABOLISM AND LONG TERM POTENTIATION

CROSS-REFERENCE TO RELATED APPLICATIONS

This application claims the benefit of U.S. Provisional Patent Application No. 61/883,433, filed on Sep. 27, 2013, U.S. Provisional Patent Application No. 62/046,953, filed on Sep. 6, 2014, and U.S. Provisional Patent Application No. 62/047,055, filed on Sep. 7, 2014, the entire disclosures of which are incorporated by reference herein for all purposes.

BACKGROUND

1. Field of the Invention

The invention relates to nutritional supplements and methods of use thereof.

2. Related Art

There has been a significant amount of research into the benefits of PDE4 inhibitors. In animal models synthetic PDE4 inhibitors have been shown to enhance object memory, and to reverse deficits to learning, working and reference memory induced by scopolamine, NMDA antagonists and under conditions of depleted tryptophan and serotonin (references 1-6).

Several articles have been published in the literature that discuss the potential of PDE4 inhibitors for cognitive enhancement in those with Alzheimer's disease, dementia, and other neurodegenerative conditions. PDE4 inhibitors have also provided improvements in performance to aged animal brains and have been shown, in animal models, to provide protection from damage from certain types of ischemic strokes. Experimental new PDE4 inhibitors are regularly being developed with the intention of treating long-term memory loss and mild cognitive impairment. Unfortunately, one of the most studied PDE4 inhibitors, rolipram, has had the side effect of emesis (vomiting) at low doses. Much work remains for developing memory enhancing PDE4 inhibitors with better side-effect profiles than rolipram (references 7-13).

SUMMARY

In one aspect, a nutritional supplement for increasing cognitive functioning in a human subject, or other mammal, is provided. The nutritional supplement includes effective amounts of a phosphodiesterase 4 (PDE4) inhibiting flavonoid and a cyclic adenosine monophosphate (cAMP) increasing labdane diterpene. In some embodiments: a) the flavonoid can be luteolin; b) the nutritional supplement can include artichoke extract as a source of the flavonoid; c) the labdane diterpene can be forskolin; d) the nutritional supplement can further include effective amounts of one or any combination of components selected from the group consisting of L-phenylalanine, L-carnitine, acetyl-L-carnitine, vitamin B6, and piperine; or e) any combination of a)-d).

In some embodiments, the nutritional supplement includes in daily dosage form about 202.5 mg to about 990 mg of artichoke extract standardized to 5% cynarin, and about 0.9 mg to about 4.4 mg of forskolin. In some embodiments: a) the nutritional supplement further includes one or any combination of components selected from the group consisting of about 180 mg to about 880 mg of acetyl-L-carnitine per daily dosage of the nutritional supplement, about 112.5 mg to about 550 mg of L-phenylalanine per daily dosage of the nutritional supplement, about 2.25 mg to about 11 mg of vitamin B6 per daily dosage of the nutritional supplement, and about 10 mg to about 20 mg of piperine per daily dosage of the nutritional supplement; b) in embodiments containing acetyl-L-carnitine, the ratio of acetyl-L-carnitine to forskolin can be about 200:1 by weight; c) particular embodiments of the nutritional supplement can include about 180 mg to about 880 mg of acetyl-L-carnitine per daily dosage of the nutritional supplement; about 112.5 mg to about 550 mg of L-phenylalanine per daily dosage of the nutritional supplement; about 2.25 mg to about 11 mg of vitamin B6 per daily dosage of the nutritional supplement; or d) any combination of a)-c). In a particular embodiment, the nutritional supplement is in capsule form, and comprises per capsule, about 300 mg of artichoke extract standardized to 5% cynarin, about 4/3 mg of forskolin, about 250 mg of acetyl-L-carnitine, about 500/3 mg of L-phenylalanine, and about 5/3 mg vitamin B6.

In a further aspect, a method of increasing cognitive functioning in a human or other mammalian subject in need thereof is provided. The method includes administering to the subject a nutritional supplement that includes therapeutically effective amounts of a phosphodiesterase 4 (PDE4) inhibiting flavonoid and a cyclic adenosine monophosphate (cAMP) increasing labdane diterpene. In some embodiments: a) the flavonoid can be luteolin; b) the nutritional supplement can include artichoke extract as a source of the flavonoid; c) the labdane diterpene can be forskolin; d) the nutritional supplement can further include therapeutically effective amounts of one or any combination of components selected from the group consisting of L-phenylalanine, L-carnitine, acetyl-L-carnitine, vitamin B6, and piperine; or e) any combination of a)-d).

In some embodiments, the method includes administering to the subject a nutritional supplement that includes in daily dosage form about 202.5 mg to about 990 mg of artichoke extract standardized to 5% cynarin, and about 0.9 mg to about 4.4 mg of forskolin. In some embodiments: a) the nutritional supplement further includes one or any combination of components selected from the group consisting of about 180 mg to about 880 mg of acetyl-L-carnitine per daily dosage of the nutritional supplement, about 112.5 mg to about 550 mg of L-phenylalanine per daily dosage of the nutritional supplement, about 2.25 mg to about 11 mg of vitamin B6 per daily dosage of the nutritional supplement, and about 10 mg to about 20 mg of piperine per daily dosage of the nutritional supplement; b) in embodiments containing acetyl-L-carnitine, the ratio of acetyl-L-carnitine to forskolin can be about 200:1 by weight; c) particular embodiments of the nutritional supplement can include about 180 mg to about 880 mg of acetyl-L-carnitine per daily dosage of the nutritional supplement; about 112.5 mg to about 550 mg of L-phenylalanine per daily dosage of the nutritional supplement; and about 2.25 mg to about 11 mg of vitamin B6 per daily dosage of the nutritional supplement; or d) any combination of a)-c). In a particular embodiment, the nutritional supplement is in capsule form, and comprises per capsule, about 300 mg of artichoke extract standardized to 5% cynarin, about 4/3 mg of forskolin, about 250 mg of acetyl-L-carnitine, about 500/3 mg of L-phenylalanine, and about 5/3 mg vitamin B6, and two to three capsules are administered per daily dosage.

In a further aspect, a nutritional supplement for increasing cognitive functioning in a human, or other mammal, is provided. The nutritional supplement includes an effective amount of means for inhibiting phosphodiesterase 4 (PDE4), an effective amount of means for increasing cyclic adenosine monophosphate (cAMP), and an effective amount of means for increasing acetylcholine. In some embodiments, the nutritional supplement also includes effective amounts of one or any combination of components selected from the group consisting of L-phenylalanine, L-carnitine, vitamin B6, and piperine.

In another aspect, a method of increasing cognitive functioning in a human or other mammalian subject in need thereof is provided. The method includes administering to the subject a nutritional supplement that includes therapeutically effective amounts of means for inhibiting phosphodiesterase 4 (PDE4), means for increasing cyclic adenosine monophosphate (cAMP), and means for increasing acetylcholine. In some embodiments, the nutritional supplement also includes effective amounts of one or any combination of components selected from the group consisting of L-phenylalanine, L-carnitine, vitamin B6, and piperine.

In a further aspect, a nutritional supplement for increasing cognitive functioning in a human, or other mammal, is provided. The nutritional supplement includes effective amounts of mesembrenone and a cyclic adenosine monophosphate (cAMP) increasing labdane diterpene. In some embodiments: a) the labdane diterpene can be forskolin; b) the nutritional supplement can further include effective amounts of one or any combination of components selected from the group consisting of L-phenylalanine, L-carnitine, acetyl-L-carnitine, vitamin B6, and piperine; or c) any combination of a)-b).

BRIEF DESCRIPTION OF THE DRAWINGS

For a more complete understanding of the present invention, reference is now made to the following descriptions taken in conjunction with the accompanying drawings, in which.

DETAILED DESCRIPTION

Postings on a Longecity forum started by the inventor under the name "Abelard Lindsay" on Sep. 26, 2011, and including postings at least up to Sep. 26, 2014, are incorporated by reference herein. The Longecity forum can be accessed on the World Wide Web at: longecity.org/forum/topic/51732-chemically-induced-ltp.

In one aspect, a nutritional supplement is provided. Embodiments of the nutritional supplement include a phosphodiesterase 4 (PDE4) inhibiting flavonoid and a cyclic adenosine monophosphate (cAMP) increasing labdane diterpene. Phosphodiesterase 4 is a member of a family of phosphodiesterase enzymes that degrade 3',5'-cyclic nucleotides including cAMP. In humans, phosphodiesterase 4 is abundant in brain tissue.

Figure 1:
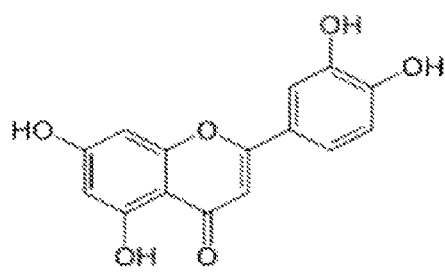
FIG. 1 is a panel showing the chemical structures of luteolin (1A) and forskolin (1B)
Figure 1:
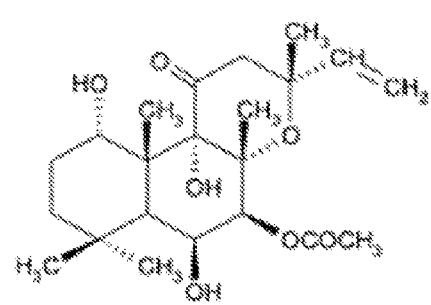
Figure 1:
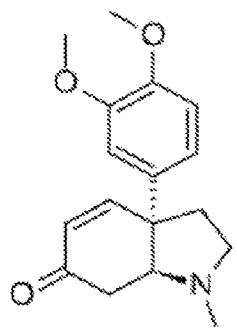
Figure 1:
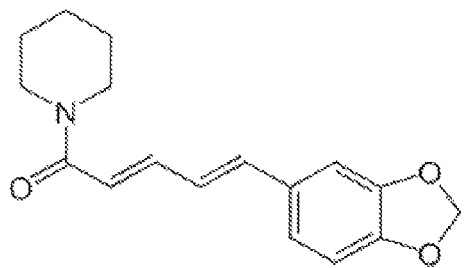

A flavonoid is a plant compound having a three ring backbone structure, including flavonoid glycosides. Luteolin, shown in FIG. 1A, is a flavonoid that can inhibit 3',5'-cyclic nucleotide phosphodiesterase enzymes, including PDE4. Luteolin is found in certain plants such as artichoke (Cynara scolymus), and artichoke extracts containing luteolin are commercially available, for example, from Now Foods, Bloomingdale, Ill., USA, Jarrow Formulas, Los Angeles, Calif., USA, and Source Naturals, Scotts Valley, Calif., USA. An artichoke extract can be standardized based upon the amount of cynarin, a caffeoylquinic acid present in artichoke.

A labdane diterpene is a natural product having a bicyclic diterpene backbone structure. Forskolin, shown in FIG. 1B, is a labdane diterpene that can stimulate the enzyme adenylyl cyclase, which catalyzes the conversion of ATP to cAMP. Forskolin is found in the plant *Coleus forskohlii*, and *Coleus forskohlii* extracts containing forskolin are commercially available, for example, from Neutraceutical, Park City, Utah, USA, and Better Body Sports, Ventura, Calif., USA. Purified forskolin preparations are also commercially available, for example, from Sigma-Aldrich Corp., St. Louis, Mo., USA.

Mesembrenone is an alkaloid PDE4 inhibitor shown in FIG. 1C. Mesembrenone is found in the succulent herb *Sceletium tortuosum*, also known as kanna, and kanna extracts containing mesembrenone are commercially available, for example, from Organic African Red Tea Imports, Los Angeles, Calif., USA, and Source Naturals, Scotts Valley, Calif., USA.

Cyclic AMP appears to play a role in long term potentiation and other nervous system processes. Combining an adenylyl cyclase stimulator with a PDE4 inhibitor can lead to enhanced cAMP production with decreased cAMP degradation, resulting in increased levels of cAMP in the body and increased intracellular cAMP levels. Thus, embodiments of the nutritional supplement can affect nervous system functioning when administered to a subject.

The nutritional supplement can be taken orally in the form of a capsule, pill or tablet, for example, and can contain pharmaceutically or physiologically acceptable carriers. For example, inert, pharmaceutically or physiologically acceptable solid carriers can be one or more substances which may also act as diluents, flavoring agents, colorizers, solubilizers, lubricants, suspending agents, or binders. The solid carrier material can also include encapsulating material. Examples of carriers include, but are not limited to. inert diluents, such as calcium carbonate, sodium carbonate, sodium citrate, lactose, calcium phosphate, sodium phosphate, microcrystalline cellulose, corn starch, potato starch, and cellulose esters such as cellulose acetate, ethyl cellulose; granulating and disintegrating agents, for example, corn starch, or alginic acid, or complex silicates; binding agents, for example starch, polyvinylpyrrolidone, PEG-8000, gelatin or gum acacia, and lubricating agents, for example magnesium stearate, stearic acid, sodium lauryl sulfate, or talc. Formulations of pharmaceutical dosage forms, such as tablets, capsules, syrups, dragees, are within the level of ordinary skill and are described in detail in Remington, The Science and Practice of Pharmacy, $22^{nd}$ Edition, Allen, Loyd V., Jr. Ed., Pharmaceutical Press (2012), incorporated herein by reference The nutritional supplement can be administered to a subject to increase or enhance cognitive functioning. Cognitive functioning refers to higher-order brain processes such as concentration, alertness, focus, attention, motivation, wakefulness, and long-term memory. An effective amount, or a therapeutically effective amount, of a substance is an amount that increases or enhances cognitive functioning in the subject.

In some cases, cognitive functioning can be assessed using cognitive tests such as long-term recall of studied material, spatial search and grammatical reasoning tests.

The subject can be a human or other mammal.

The primary means by which PDE4 inhibitors are theorized to improve learning and memory is by lengthening the duration during which the secondary messenger cyclic-adenosine monophosphate (cAMP) is present in cells, where it can activate the cAMP response element binding protein CREB and thus increase CREB's gene transcription activities in the nucleus and mitochondria. These gene transcription activities are what are theorized to lead to long term potentiation (LTP) activity which is crucial to learning and memory. Additionally, increased transcription of brain-derived neurotrophic factor (BDNF) by CREB has been linked to improved short-term memory in studies (references 14-20).

Forskolin is a chemical derived from the plant *Coleus forskohlii* which has been widely used in traditional Ayurvedic medicine. It has also has been extensively studied due to its ability to increase levels of intracellular cAMP (references 21-23).

Luteolin can inhibit the family of phosphodiesterase enzymes (PDE 1 through 5) that degrade 3',5'-cyclic nucleotides. Inhibition of phosphodiesterase 1 and phosphodiesterase 5 have both shown beneficial activity with regard to synaptic plasticity (references 24-27). PDE 4 specific inhibitors are also known, such as rolipram (reference 28).

CREB's activities in the cell have been shown to increase the transcription of enzymes which are key enzymes in dopamine metabolism, such as tyrosine hydroxylase. Increased transcription of these enzymes leads to increased processing of dopamine precursors. The essential amino acid L-phenylalanine is converted into L-tyrosine by phenylalanine hydroxylase and then converted into L-dopa by tyrosine hydroxylase. Vitamin B6 can support the conversion of L-dopa to dopamine by dopa decarboxylase (references 29-32). Thus, L-phenylalanine and/or Vitamin B6 can be added to embodiments of the nutritional supplement.

Some embodiments of the nutritional supplement may lead to afternoon sleepiness and a temporary decrease in short term memory. Studies have provided evidence that forskolin increases transcription of the enzyme acetylcholinesterase. Acetylcholinesterase breaks down acetylcholine in the brain. Sleepiness is a common symptom of medicines that are anticholinergic so it would follow that excess acetylcholinesterase could lead to lower acetylcholine levels and thus sleepiness. Acetyl-L-carnitine has been shown to increase the levels of acetylcholine in the brain and thus could be helpful in counteracting increased transcription of acetylcholinesterase by forskolin (references 33-35). Thus, acetyl-L-carnitine can be added to the nutritional supplement. In embodiments containing acetyl-L-carnitine, afternoon drowsiness and short-term memory issues can be largely mitigated.

Kanna extract and mesembrenone have been shown to significantly inhibit PDE4 (reference 38). Embodiments containing kanna extract were found by the inventor to be effective at increasing cognitive functioning, although less beneficial than artichoke extract.

In particular embodiments, multiple components are combined to create a synergistic combination for improving synaptic and cognitive functions in the mammalian brain. These components include: a cyclic adenosine monophosphate (cAMP) increasing labdane diterpene such as forskolin; a PDE4 inhibiting flavonoid such as Luteolin contained within artichoke extract; the amino acid L-phenylalanine; vitamin B6; and the quaternary ammonium compound L-carnitine or its acylated derivative acetyl-L-carnitine.

Figure 2:
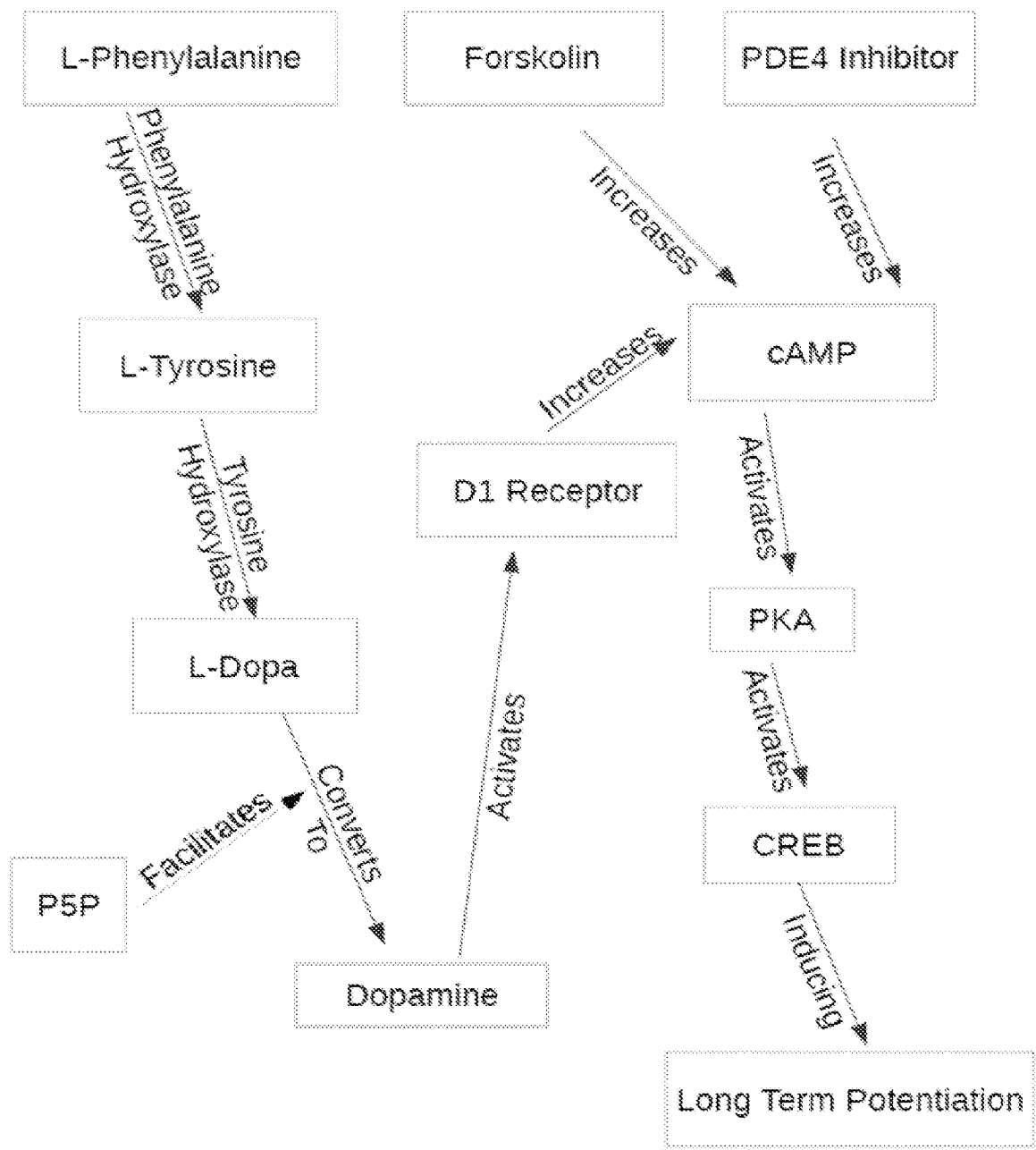
FIG. 2 is a diagram showing suggested interactions of components of a nutritional supplement.

Although not wishing to be bound by theory, it is believed that when these components are taken together orally in the form of a nutritional supplement, PDE-4 is inhibited and cAMP is increased leading to sustained activation of CREB (cAMP response element binding protein), which helps to maintain effective long-term potentiation (LTP) and thus memory. In addition, L-phenylalanine is believed to provide adequate precursors to the dopaminergic metabolic pathway to accommodate upregulation of tyrosine hydroxylase by PDE4 inhibition, and vitamin B6 is believed to behave as a dopamine metabolic co-factor (see FIG. 2). Also, L-carnitine and acetyl-L-carnitine are believed to counteract the upregulation of acetylcholinesterase caused by forskolin. Thus, it is believed that the dopamine co-factors provide a steady supply of co-factors to the enhanced D1/PKA/DARPP-32 signaling cascade caused by PDE-4 inhibition and the subsequent increase in dopamine synthesis and turnover due to increases in tyrosine hydroxylase gene transcription (references 36-45).

Some particular embodiments for an adult human that have been determined through experimentation include:
  200 mg acetyl-L-carnitine;
  1 mg forskolin;
  225 mg artichoke extract standardized to 5% cynarin;
  125 mg L-phenylalanine; and
  2.5 mg vitamin B6.
Alternative formulas include:
  200 mg acetyl-L-carnitine
  1 mg forskolin
  225 mg artichoke extract standardized to 5% cynarin;
or
  1 mg forskolin
  225 mg artichoke extract standardized to 5% cynarin
  125 mg L-phenylalanine These particular embodiments are exemplary and the weight of each ingredient may be varied by 10% without significant degradation of efficacy. Also, from 1 to 2, 1 to 3, 1 to 4, 2 to 3, 2 to 4, 3 to 4, or 1, 2, 3 or 4 doses may be taken per day. Thus, in some embodiments, the range of ingredients per daily dosage can be:
  about 202.5 mg to about 495 mg, about 202.5 mg to about 742.5 mg, or about 202.5 mg to about 990 mg artichoke extract standardized to 5% cynarin; and
  about 0.9 mg to about 2.2 mg, about 0.9 mg to about 3.3 mg, or about 0.9 mg to about 4.4 mg forskolin.

Alternatively, the daily dosage can be about 225 mg, about 450 mg, about 675 mg or about 900 mg artichoke extract standardized to 5% cynarin; and about 1 mg, about 2 mg, about 3 mg, or about 4 mg forskolin, or can be varied by 10% of such amounts.

Further, in some embodiments, the nutritional supplement can include one or a combination of the following ingredients, in ranges per daily dosage:
  about 180 mg to about 440 mg, about 180 mg to about 660 mg, or about 180 mg to about 880 mg acetyl-L-carnitine;
  about 112.5 mg to about 275 mg, about 112.5 mg to about 412.5 mg, or about 112.5 mg to about 550 mg L-phenylalanine; and
  about 2.25 mg to about 5.5 mg, about 2.25 mg to about 8.25 mg, or about 2.25 mg to about 11 mg vitamin B6.

Alternatively, the daily dosage can be about 200 mg, about 400 mg, about 600 mg, or about 800 mg acetyl-L-carnitine; about 125 mg, about 250 mg, about 375 mg, or about 500 mg L-phenylalanine; and about 2.5 mg, about 5 mg, about 7.5 mg, or about 10 mg vitamin B6, or can be varied by 10% of such amounts.

The alkaloid piperine (FIG. 1D) can also be included as a component of the nutritional supplement. Piperine is present in black pepper and has been used in nutritional products to enhance the bioavailability of flavonoids by blocking glucuronidation in the liver and digestive tract. Piperine has been found to enhance the bioavailability of curcumin by 2000%, and enhance the bioavailability of resveratrol (references 46-47). In embodiments of the nutritional supplement, piperine can be included in the range of about 10 mg to about 20 mg per daily dosage of the nutritional supplement. Piperine can be obtained commercially, for example, from Sigma-Aldrich Corp., St. Louis, Mo., USA.

Additional inactive ingredients such as different types of color, filler, binder, capsule, and coating are permissible. Formulations of pharmaceutical dosage forms, such as tablets, capsules, syrups, dragees, are within the level of ordinary skill and are described in detail in Remington, The Science and Practice of Pharmacy, 22$^{nd}$ Edition, Allen, Loyd V., Jr. Ed., Pharmaceutical Press (2012), incorporated herein by reference In embodiments containing acetyl-L-carnitine, a ratio of acetyl-L-carnitine to forskolin of about 200:1 by weight provides particularly good effects on cognitive functioning.

Forskolin in the amount of 1-4 mg per daily dosage is less than the amount typically provided in forskolin supplements (25 mg to 50 mg). The 1-4 mg daily dosage was found by the inventor to provide positive cognitive benefits, while larger amounts produced side effects and diminished or eliminated cognitive benefits.

In a particular embodiment, a capsule of the nutritional supplement comprises about 250 mg acetyl-L-carnitine; about 4/3 mg forskolin; about 300 mg artichoke extract standardized to 5% cynarin; about 500/3 mg L-phenylalanine; and about 5/3 mg vitamin B6. From 2-3 capsules can be taken per day. Two capsules can be taken on an empty stomach immediately upon waking, with no more than 3 capsules taken per day.

As used herein, the term "about" in reference to an amount of a substance indicates an amount within experimental error.

It is to be understood that the ranges and limits mentioned herein include all sub-ranges located within the prescribed limits, inclusive of the limits themselves unless otherwise stated.

The present invention may be better understood by referring to the accompanying examples, which are intended for illustration purposes only and should not in any sense be construed as limiting the scope of the invention.

EXAMPLE 1

Artichoke Extract and Forskolin

The inventor ingested 900 mg artichoke extract standardized to 5% cynarin (Now Foods, Bloomingdale, Ill.) and 385 mg *Coleus forskhohlii* root standardized to 1% forskolin yielding 3.85 mg forskolin (Neutraceutical, Park City, Utah). The combination was administered once per morning. After taking the combination, the inventor performed better on spatial search and grammatical reasoning tests compared to baseline. The inventor felt increased motivation and could study for longer periods of time. He also had subjectively better recall of material that was studied. The inventor experienced excessive tiredness in the afternoon, and short term memory, as measured by a paired-associate-learning test "Paired Associates" (Cambridge Brain Sciences, Ontario, Canada) in which a pair of items is learned (an object and its location), was slightly negatively affected.

EXAMPLE 2

Artichoke Extract, Forskolin and L-Phenylalanine

The inventor ingested artichoke extract and forskolin as in Example 1, and also ingested up to 1500 mg L-Phenylalanine (Now Foods, Bloomingdale, Ill.). The combination was administered once per morning. After taking the combination, the inventor performed better on spatial search and grammatical reasoning tests compared to baseline, felt increased motivation, could study for longer periods of time, and had subjectively better recall of material that was studied. Compared to the combination containing just artichoke extract and forskolin, the inventor experienced less tiredness in the afternoon. Short term memory, as measured by the paired-associate-learning test "Paired Associates" (Cambridge Brain Sciences, Ontario, Canada), was slightly negatively affected.

EXAMPLE 3

Artichoke Extract, Forskolin, L-Phenylalanine and Vitamin B6

The inventor ingested artichoke extract, forskolin and L-phenylalanine as in Example 2, and also ingested 5 mg vitamin B6 as part of a B vitamin complex (Neutraceutical, Park City, Utah). The combination was administered once per morning. After taking the combination, the inventor performed better on spatial search and grammatical reasoning tests compared to baseline, felt increased motivation, could study for longer periods of time, and had subjectively better recall of material that was studied. The inventor experienced less tiredness in the afternoon and the effects of the stack did not diminish over several days of taking it. Short term memory, as measured by the paired-associate-learning test "Paired Associates" (Cambridge Brain Sciences, Ontario, Canada), was slightly negatively affected.

EXAMPLE 4

Artichoke Extract, Forskolin, L-Phenylalanine, Vitamin B6 and Acetyl-L-Carnitine The inventor ingested artichoke extract, forskolin, L-phenylalanine and vitamin B6 as in Example 3, and also ingested 750 mg of acetyl-L-carnitine (Primaforce, Burlington, N.C.). The combination was administered once per morning. After taking the combination, the inventor performed better on spatial search and grammatical reasoning tests compared to baseline, felt increased motivation, could study for longer periods of time, and had subjectively better recall of material that was studied. The inventor experienced no tiredness in the afternoon. The amount of acetyl-L-carnitine relative to forskolin was increased until the inventor's paired associates scores no longer fell after taking the combination.

EXAMPLE 5

This example is based on a testimonial by a subject. The subject was a female with concentration and memory problems. The nutritional supplement was in capsular form, with a capsule including 300 mg artichoke extract standardized to 5% cynarin, ~4/3 mg forskolin, 500/3 mg L-phenylalanine, 5/3 mg vitamin B6, and 250 mg acetyl-L-carnitine. Also included were cellulose, vegetable stearate and silica as carriers. After taking the nutritional supplement, the subject reported increased focus, energy and memory.

EXAMPLE 6

This example is based on a testimonial by a male subject. The nutritional supplement was in capsular form, with a capsule including 300 mg artichoke extract standardized to 5% cynarin, ~4/3 mg forskolin, 500/3 mg L-phenylalanine, 5/3 mg vitamin B6, and 250 mg acetyl-L-carnitine. Also included were cellulose, vegetable stearate and silica as carriers. After taking the nutritional supplement, the subject reported increased focus and mental vision.

EXAMPLE 7

This example is based on a testimonial by a male subject. The nutritional supplement was in capsular form, with a capsule including 300 mg artichoke extract standardized to 5% cynarin, ~4/3 mg forskolin, 500/3 mg L-phenylalanine, 5/3 mg vitamin B6, and 250 mg acetyl-L-carnitine. Also included were cellulose, vegetable stearate and silica as carriers. After taking the nutritional supplement, the subject reported increased focus and concentration.

EXAMPLE 8

The inventor ingested 25 mg kanna extract (Zembrin®, Organic African Red Tea Imports, Los Angeles, Calif.), 1500 mg L-phenylalanie, and 4 mg forskolin (Better Body Sports LLC, Ventura, Calif.). This combination was administered once per morning. After taking the combination, the inventor obtained much better scores on "Polygons" and "Odd One Out" tests (Cambridge Brain Sciences, Ontario, Canada). Studying was much easier and more enjoyable.

REFERENCES

The following publications are incorporated by reference herein:
1. Rutten K, Van donkelaar E L, Ferrington L, et al. Phosphodiesterase inhibitors enhance object memory independent of cerebral blood flow and glucose utilization in rats. Neuropsychopharmacology. 2009; 34(8):1914-25. PMID 19262466.
2. Egawa T, Mishima K, Matsumoto Y, Iwasaki K, Iwasaki K, Fujiwara M. Rolipram and its optical isomers, phosphodiesterase 4 inhibitors, attenuated the scopolamine-induced impairments of learning and memory in rats. Jpn J Pharmacol. 1997; 75(3):275-81. PMID 9434259.
3. Zhang H T, O'donnell J M. Effects of rolipram on scopolamine-induced impairment of working and reference memory in the radial-arm maze tests in rats. Psychopharmacology (Berl). 2000; 150(3):311-6. PMID 10923759.
4. Zhang H T, Crissman A M, Dorairaj N R, Chandler L J, O'donnell J M Inhibition of cyclic AMP phosphodiesterase (PDE4) reverses memory deficits associated with NMDA receptor antagonism. Neuropsychopharmacology. 2000; 23(2):198-204. PMID 10882846.
5. Zhang H T, Huang Y, Suvarna N U, et al. Effects of the novel PDE4 inhibitors MEM1018 and MEM1091 on memory in the radial-arm maze and inhibitory avoidance tests in rats. Psychopharmacology (Berl). 2005; 179(3): 613-9. PMID 15672274.
6. Mclean J H, Smith A, Rogers S, Clarke K, Darby-king A, Harley C W. A phosphodiesterase inhibitor, cilomilast, enhances cAMP activity to restore conditioned odor preference memory after serotonergic depletion in the neonate rat. Neurobiol Learn Mem. 2009; 92(1):63-9. PMID 19233302.
7. Wang C, Yang X M, Zhuo Y Y, et al. The phosphodiesterase-4 inhibitor rolipram reverses Aβ-induced cognitive impairment and neuroinflammatory and apoptotic responses in rats. Int J Neuropsychopharmacol. 2012; 15(6):749-66. PMID 21733236.
8. Rose G M, Hopper A, De vivo M, Tehim A. Phosphodiesterase inhibitors for cognitive enhancement. Curr Pharm Des. 2005; 11(26):3329-34. PMID 16250839.
9. Drott J, Desire L, Drouin D, Pando M, Haun F. Etazolate improves performance in a foraging and homing task in aged rats. Eur J Pharmacol. 2010; 634(1-3):95-100. PMID 20223232.
10. Li L X, Cheng Y F, Lin H B, Wang C, Xu J P, Zhang H T. Prevention of cerebral ischemia-induced memory deficits by inhibition of phosphodiesterase-4 in rats. Metab Brain Dis. 2011; 26(1):37-47. PMID 21327879.
11. Gallant M, Aspiotis R, Day S, et al. Discovery of MK-0952, a selective PDE4 inhibitor for the treatment of long-term memory loss and mild cognitive impairment. Bioorg Med Chem Lett. 2010; 20(22):6387-93. PMID 20933411.
12. Heaslip R J, Evans D Y. Emetic, central nervous system, and pulmonary activities of rolipram in the dog. Eur J Pharmacol. 1995; 286(3):281-90. PMID 8608790.
13. Bruno 0, Fedele E, Prickaerts J, et al. GEBR-7b, a novel PDE4D selective inhibitor that improves memory in rodents at non-emetic doses. Br J Pharmacol. 2011; 164 (8):2054-63. PMID 21649644.
14. Mackenzie S J, Houslay M D. Action of rolipram on specific PDE4 cAMP phosphodiesterase isoforms and on the phosphorylation of cAMP-response-element-binding protein (CREB) and p38 mitogen-activated protein (MAP) kinase in U937 monocytic cells. Biochem J. 2000; 347(Pt 2):571-8. 10749688.
15. Xu W, Kasper L H, Lerach S, Jeevan T, Brindle P K. Individual CREB-target genes dictate usage of distinct cAMP-responsive coactivation mechanisms. EMBO J. 2007; 26(12):2890-903. PMID 17525731.
16. Benito E, Valor L M, Jimenez-minchan M, Huber W, Barco A. cAMP response element-binding protein is a primary hub of activity-driven neuronal gene expression. J Neurosci. 2011; 31(50):18237-50. PMID 22171029.
17. Lee J, Kim C H, Simon D K, et al. Mitochondrial cyclic AMP response element-binding protein (CREB) mediates mitochondrial gene expression and neuronal survival. J Biol Chem. 2005; 280(49):40398-401. PMID 16207717.
18. Deisseroth K, Bito H, Tsien R W. Signaling from synapse to nucleus: postsynaptic CREB phosphorylation during multiple forms of hippocampal synaptic plasticity. Neuron. 1996; 16(1):89-101. PMID 8562094.
19. Kida S. A Functional Role for CREB as a Positive Regulator of Memory Formation and LTP. Exp Neurobiol. 2012; 21(4):136-40. PMID 23319873.
20. Suzuki A, Fukushima H, Mukawa T, et al. Upregulation of CREB-mediated transcription enhances both short- and long-term memory. J Neurosci. 2011; 31(24):8786-802. PMID 21677163.
21. Ammon H P, Müller A B. Forskolin: from an ayurvedic remedy to a modern agent. Planta Med. 1985; 51(6):473-7. PMID 17345261.
22. Seamon K B, Daly J W. Forskolin: a unique diterpene activator of cyclic AMP-generating systems. J Cyclic Nucleotide Res. 1981; 7(4):201-24. PMID 6278005.
23. Barad M, Bourtchouladze R, Winder D G, Golan H, Kandel E. Rolipram, a type IV-specific phosphodiesterase inhibitor, facilitates the establishment of long-lasting long-term potentiation and improves memory. Proc Natl Acad Sci USA. 1998; 95(25):15020-5. PMID 9844008.
24. Brown J E, Rice-evans CA. Luteolin-rich artichoke extract protects low density lipoprotein from oxidation in vitro. Free Radic Res. 1998; 29(3):247-55. PMID 9802556.
25. Yu M C, Chen J H, Lai C Y, Han C Y, Ko W C. Luteolin, a non-selective competitive inhibitor of phosphodiesterases 1-5, displaced [3H]-rolipram from high-affinity rolipram binding sites and reversed xylazine/ketamine-induced anesthesia. Eur J Pharmacol. 2010; 627(1-3):269-75. PMID 19853596.
26. Kitagawa Y, Hirano T, Kawaguchi S Y. Prediction and validation of a mechanism to control the threshold for inhibitory synaptic plasticity. Mol Syst Biol. 2009; 5:280. PMID 19536203.
27. Puzzo D, Sapienza S, Arancio O, Palmeri A. Role of phosphodiesterase 5 in synaptic plasticity and memory. Neuropsychiatr Dis Treat. 2008; 4(2):371-87. PMID 18728748.
28. Otmakhov N, Khibnik L, Otmakhova N, et al. Forskolin-induced LTP in the CA1 hippocampal region is NMDA receptor dependent. J Neurophysiol. 2004; 91(5):1955-62. PMID 14702333.
29. Piech-dumas KM, Tank A W. CREB mediates the cAMP-responsiveness of the tyrosine hydroxylase gene: use of an antisense RNA strategy to produce CREB-deficient PC12 cell lines. Brain Res Mol Brain Res. 1999; 70(2):219-30. PMID 10407170.
30. Kumer S C, Vrana K E. Intricate regulation of tyrosine hydroxylase activity and gene expression. J Neurochem. 1996; 67(2):443-62. PMID 8764568.
31. Slominski A, Zmijewski M A, Pawelek J. L-tyrosine and L-dihydroxyphenylalanine as hormone-like regulators of melanocyte functions. Pigment Cell Melanoma Res. 2012; 25(1):14-27. PMID 21834848.
32. Amadasi A, Bertoldi M, Contestabile R, et al. Pyridoxal 5'-phosphate enzymes as targets for therapeutic agents. Curr Med Chem. 2007; 14(12):1291-324. PMID 17504214.
33. Curtin B F, Pal N, Gordon R K, Nambiar M P. Forskolin, an inducer of cAMP, up-regulates acetylcholinesterase expression and protects against organophosphate exposure in neuro 2A cells. Mol Cell Biochem. 2006; 290(1-2):23-32. PMID 16924422.
34. Hartvig P, Lindström B, Pettersson E, Wiklund L. Reversal of postoperative somnolence using a two-rate infusion of physostigmine. Acta Anaesthesiol Scand. 1989; 33(8): 681-5. PMID 2589000.
35. White H L, Scates P W. Acetyl-L-carnitine as a precursor of acetylcholine. Neurochem Res. 1990; 15(6):597-601. PMID 2215852.
36. Alasbahi R H, Melzig M F. (2012) "Forskolin and derivatives as tools for studying the role of cAMP." Pharmazie. 2012 January; 67(1):5-13. PMID: 22393824.
37. Yu M C, Chen J H, Lai C Y, Han C Y, Ko W C. (2010) "Luteolin, a non-selective competitive inhibitor of phosphodiesterases 1-5, displaced [3H]-rolipram from high-affinity rolipram binding sites and reversed xylazine/ketamine-induced anesthesia." Eur J Pharmacol. 2010 Feb. 10; 627(1-3):269-75. doi: 10.1016/j.ejphar.2009.10.031. Epub 2009 Oct. 22 PMID: 19853596.
38. Harvey A L, Young L C, Viljoen A M, Gericke N P. (2011) "Pharmacological actions of the South African medicinal and functional food plant Sceletium tortuosum and its principal alkaloids." J Ethnopharmacol. 2011 Oct. 11; 137(3): 1124 9. doi:10.1016/j.jep.2011.07.035. Epub 2011 Jul. 20. PMID: 21798331.
39. Dwight E. Matthews (2008) "An Overview of Phenylalanine and Tyrosine Kinetics in Humans" J Nutr. Author manuscript; available in PMC 2008 Mar. 17. Published in final edited form as: J Nutr. 2007 June; 137(6 Suppi 1):15495-1575S.PMCID: PMC2268015.
40. Lichtstein H C, Gunsalus I C, Umbreit W W (1945). "Function of the vitamin B6 group; pyridoxal phosphate (codecarboxylase) in transamination" (PDF). J Bioi Chem. 161 (1): 311-20.PMID 21005738.
41. Rani P J, Panneerselvam C. (2001). "Protective efficacy of L-carnitine on acetylcholinesterase activity in aged rat brain." J Gerontal A Bioi Sci Med Sci. 2001 March; 56(3): B140-1.PMID: 11253151.
42. Villa R F, Ferrari F, Gorini A. (2013) "ATP-ases of synaptic plasma membranes in striatum: Enzymatic systems for synapses functionality by in vivo administration of 1-acetylcarnitine in relation to Parkinson's Disease." Neuroscience. 2013 Jun. 25; 248C:414-426. doi: 10.1016/j.neuroscience.2013.06.027. [Epub ahead of print] PMID: 23806723.
43. Curtin B F, Pal N, Gordon R K, Nambiar M P. (2006). "Forskolin, an inducer of cAMP, upregulates acetylcholinesterase expression and protects against organophosphate exposure in neuro 2A cells" Mol Cell Biochem. 2006 October; 290(1-2):23-32. Epub 2006 Aug. 19. PMID 16924422.
44. Gong B, Vitolo O V, Trinchese F, Liu S, Shelanski M, Arancio 0., (2004) "Persistent improvement in synaptic and cognitive functions in an Alzheimer mouse model after rolipram treatment." J Clin Invest. 2004 December; 114 (11):1624-34. PMID: 15578094.
45. Voisin P, Bernard M. (2013) "Cyclic A M P-dependent regulation of tyrosine hydroxylase mRNA and immunofluorescence levels in rat retinal precursor cells." Cell Tissue Res. 2013 May; 352(2):207-16. doi: 10.1007/s00441-013-1555-4. Epub 2013 Jan. 26. PMID: 2335501.
46. Shoba G, Joy D, Joseph T, Majeed M, Rajendran R, Srinivas P S. Influence of piperine on the pharmacokinetics of curcumin in animals and human volunteers. Planta Med. 1998; 64(4):353-6. PMID 9619120.
47. Johnson J J, Nihal M, Siddiqui 1A, et al. Enhancing the bioavailability of resveratrol by combining it with piperine. Mol Nutr Food Res. 2011; 55(8):1169-76. PMID 21714124.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A nutritional supplement for increasing cognitive functioning in a human subject, comprising effective amounts of a phosphodiesterase 4 (PDE4) inhibiting flavonoid, a cyclic adenosine monophosphate (cAMP) increasing labdane diterpene in the form of forskolin, and acetyl-L-carnitine, wherein the nutritional supplement comprises
   about 202.5 mg to about 247.5 mg of artichoke extract standardized to 5% cynarin, as a source of the PDE4 inhibiting flavonoid, per about 0.9 mg to about 1.1 mg of the forskolin, and
   about 180 mg to about 220 mg of the acetyl-L-carnitine per about 0.9 mg to about 1.1 mg of the forskolin.

2. The nutritional supplement of claim 1, further comprising effective amounts of one or any combination of components selected from the group consisting of L-phenylalanine, L-carnitine, vitamin B6, and piperine.

3. The nutritional supplement of claim 1, further comprising an effective amount of piperine.

4. The nutritional supplement of claim 1, further comprising an effective amount of L-phenylalanine.

5. The nutritional supplement of claim 1, further comprising an effective amount of vitamin B6.

6. The nutritional supplement of claim 1, further comprising one or any combination of components selected from the group consisting of about 112.5 mg to about 137.5 mg of L-phenylalanine per about 0.9 mg to about 1.1 mg of the forskolin, and an effective amount of vitamin B6.

7. The nutritional supplement of claim 1, wherein the ratio of acetyl-L-carnitine to forskolin is about 200:1 by weight.

8. The nutritional supplement of claim 1, further comprising L-phenylalanine in an amount of about 112.5 mg to about 137.5 mg per about 0.9 to about 1.1 mg of the forskolin.

9. The nutritional supplement of claim 8, wherein the artichoke extract is in an amount of about 225 mg per about 1 mg of the forskolin, the acetyl-L-carnitine is in an amount of about 180 mg to about 220 mg per about 1 mg of the forskolin, and the L-phenylalanine is in an amount of about 125 mg per about 1 mg of the forskolin.

10. A nutritional supplement for increasing cognitive functioning in a human subject, comprising in daily dosage form
about 900 mg of artichoke extract standardized to 5% cynarin, as a source of a phosphodiesterase 4 inhibiting flavonoid,
about 4 mg of forskolin,
about 720 mg to about 880 mg of acetyl-L-carnitine, and
about 500 mg of L-phenylalanine.

11. A nutritional supplement for increasing cognitive functioning in a human subject, consisting essentially of effective amounts of
artichoke extract standardized to 5% cynarin, as a source of a phosphodiesterase 4 inhibiting flavonoid,
a cyclic adenosine monophosphate increasing labdane diterpene in the form of forskolin,
acetyl-L-carnitine,
L-phenylalanine,
vitamin B6,
and inactive ingredients,
wherein the artichoke extract is in an amount of about 202.5 mg to about 247.5 mg per about 0.9 mg to about 1.1 mg of the forskolin, the acetyl-L-carnitine is in an amount of about 180 mg to about 220 mg per about 0.9 mg to about 1.1 mg of the forskolin, and the L-phenylalanine is in an amount of about 112.5 mg to about 137.5 mg per about 0.9 to about 1.1 mg of the forskolin.

12. The nutritional supplement of claim 11, wherein the artichoke extract is in an amount of about 225 mg per about 1 mg of the forskolin, the acetyl-L-carnitine is in an amount of about 180 mg to about 220 mg per about 1 mg of the forskolin, and the L-phenylalanine is in an amount of about 125 mg per about 1 mg of the forskolin.

13. A nutritional supplement for increasing cognitive functioning in a human subject, consisting essentially of, in daily dosage form,
about 900 mg of artichoke extract standardized to 5% cynarin, as a source of a phosphodiesterase 4 inhibiting flavonoid,
about 4 mg of forskolin,
about 720 mg to about 880 mg of acetyl-L-carnitine,
about 500 mg of L-phenylalanine,
an effective amount of vitamin B6,
and inactive ingredients.

\* \* \* \* \*